(12) United States Patent
Viavattine (10) Patent No.: US 8,236,442 B2
(45) Date of Patent: Aug. 7, 2012

(54) ASYMMETRIC APERTURE PATTERN IN A CURRENT COLLECTOR FOR AN ELECTROCHEMICAL CELL

(75) Inventor: Joseph J. Viavattine, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 164 days.

(21) Appl. No.: 12/023,776

(22) Filed: Jan. 31, 2008

(65) Prior Publication Data

US 2009/0197157 A1    Aug. 6, 2009

(51) Int. Cl.
*H01M 4/08* (2006.01)
(52) U.S. Cl. .................. 429/120; 429/209; 29/623.1
(58) Field of Classification Search .................. 429/120
See application file for complete search history.

(56) References Cited

U.S. PATENT DOCUMENTS

| | | | |
|---|---|---|---|
| 4,477,546 A | 10/1984 | Wheeler et al. | |
| 5,849,430 A * | 12/1998 | Lee | 429/94 |
| 6,582,855 B1 * | 6/2003 | Miyamoto et al. | 429/235 |
| 6,680,141 B2 | 1/2004 | Hikmet et al. | |
| 6,893,777 B2 | 5/2005 | Probst | |
| 7,000,297 B2 | 2/2006 | Frustaci et al. | |
| 7,138,210 B2 | 11/2006 | Kim et al. | |
| 2002/0146625 A1* | 10/2002 | Probst | 429/241 |
| 2003/0104281 A1* | 6/2003 | Frustaci et al. | 429/241 |
| 2006/0110661 A1 | 5/2006 | Lee et al. | |
| 2006/0210880 A1* | 9/2006 | Howard et al. | 429/241 |

* cited by examiner

*Primary Examiner* — Patrick Ryan
*Assistant Examiner* — Brent Thomas
(74) *Attorney, Agent, or Firm* — Carol F. Barry (57) ABSTRACT

An electrode for an electrochemical cell in an implantable medical device is presented. The electrode comprises a current collector with electrode material disposed thereon. The current collector includes an asymmetric aperture pattern that uniformly dissipates heat during current flow through the current collector.

11 Claims, 14 Drawing Sheets

ASYMMETRIC APERTURE PATTERN IN A CURRENT COLLECTOR FOR AN ELECTROCHEMICAL CELL

CROSS-REFERENCE TO RELATED APPLICATION

The present application claims priority and other benefits from U.S. application Ser. No. 11/701,329 filed Jan. 31, 2007, and requested to be converted to a provisional application on Jan. 30, 2008, the disclosure of which is incorporated herein by reference in its entirety.

FIELD OF THE INVENTION

The present invention generally relates to an electrochemical cell for an implantable medical device, and, more particularly, to a current collector used in an electrode for an electrochemical cell.

BACKGROUND OF THE INVENTION

Implantable medical devices (IMDs) detect and deliver therapy for a variety of medical conditions in patients. IMDs include implantable pulse generators (IPGs) or implantable cardioverter-defibrillators (ICDs) that deliver electrical stimuli to tissue of a patient. ICDs typically comprise, inter alia, a control module, a capacitor, and a battery that are housed in a hermetically sealed container. When therapy is required by a patient, the control module signals the battery to charge the capacitor, which in turn discharges electrical stimuli to tissue of a patient.

The battery includes a case, a liner, an electrode assembly, and electrolyte. The liner insulates the electrode assembly from the case. The electrode assembly includes electrodes, an anode and a cathode, with a separator therebetween. For a flat plate battery, an anode comprises a set of anode electrode plates with a set of tabs extending therefrom. The set of tabs are electrically connected. Each anode electrode plate includes a current collector with anode material disposed thereon. A cathode is similarly constructed. Electrolyte, introduced to the electrode assembly via a fill port in the case, is a medium that facilitates ionic transport and forms a conductive pathway between the anode and cathode.

Heat generated during discharge of the battery can result in high localized current densities in each current collector. It is desirable to overcome high localized current densities in current collectors.

BRIEF DESCRIPTION OF THE DRAWINGS

The present invention will become more fully understood from the detailed description and the accompanying drawings, wherein.

DETAILED DESCRIPTION

The following description of embodiments is merely exemplary in nature and is in no way intended to limit the invention, its application, or uses. For purposes of clarity, the same reference numbers are used in the drawings to identify similar elements.

One embodiment of the present invention is directed to a battery in an implantable medical device (IMD). The battery includes an electrode assembly that comprises a set of electrode plates. Each electrode plate includes a current collector with electrode material (also referred to as active material) disposed thereon. The current collector includes a conductive layer that has a first surface and a second surface with a set of apertures that extend therethrough. In one embodiment, the apertures are the same size. The apertures in the current collector form an asymmetric pattern. The asymmetric pattern of same sized apertures uniformly dissipates heat when a battery discharges. Specifically, asymmetric pattern of apertures optimizes the local current density in the current collector so that "hot spots" or areas of high current density can be reduced or eliminated. An optimized current collector could be configured with a reduced thickness compared to conventional current collectors. An optimized current collector can also result in lower current collector resistances, which reduces the overall battery resistance. Consequently, the asymmetric pattern of apertures with optimized spacing can result in lower electrode (i.e. anode and cathode) areas and thus lower battery volumes.

Figure 1:
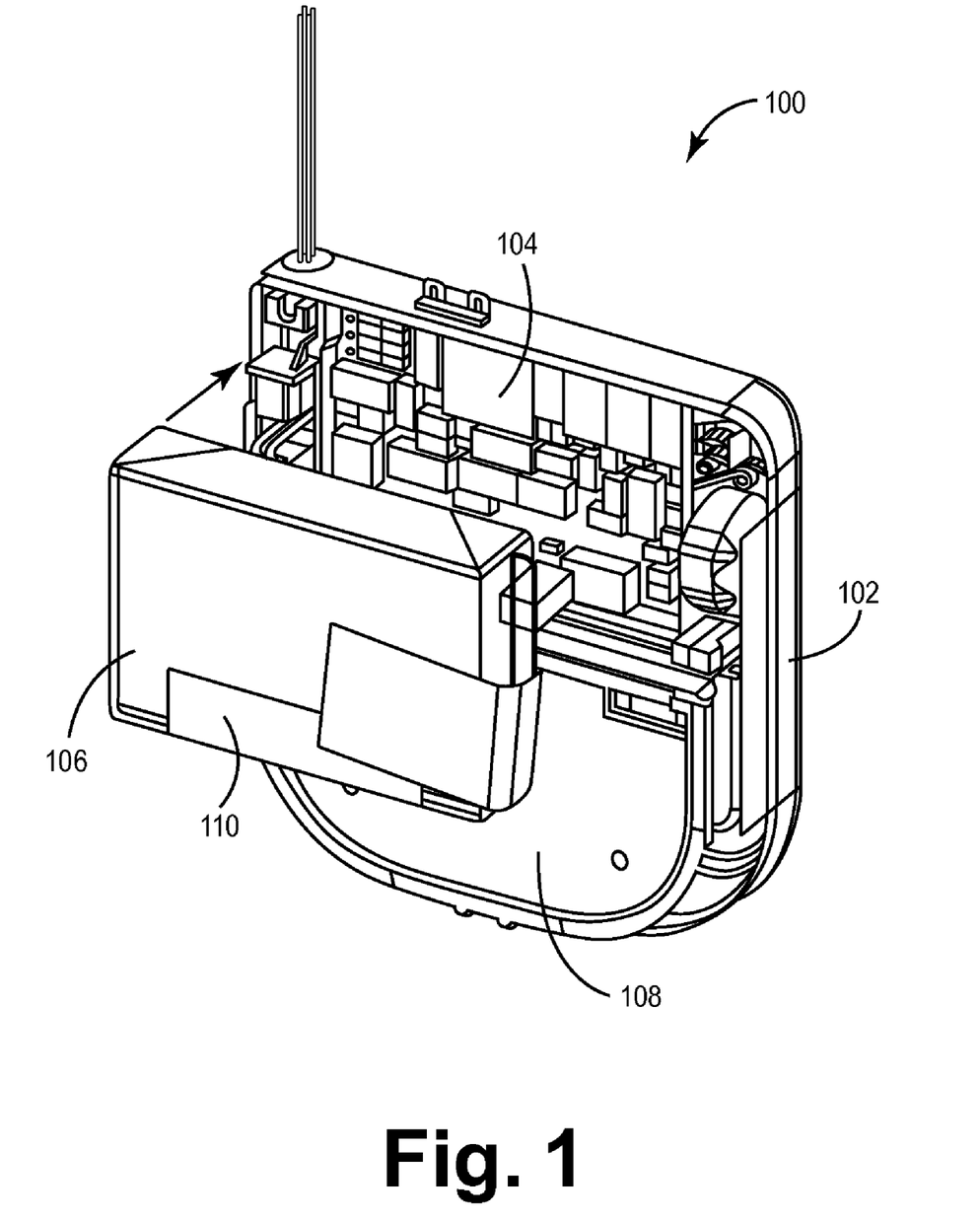
FIG. 1 is a cutaway perspective view of an implantable medical device (IMD)

FIG. 1 depicts an IMD 100 (e.g. implantable cardioverter-defibrillators (ICDs) etc.). IMD 100 includes a case 102, a control module 104, a battery 106 (e.g. organic electrolyte battery etc.) and capacitor(s) 108. Control module 104 controls one or more sensing and/or stimulation processes from IMD 100 via leads (not shown). Battery 106 includes an insulator 110 (or liner) disposed therearound. Battery 106 charges capacitor(s) 108 and powers control module 104.

FIGS. 2 through 5 depict details of an exemplary organic electrolyte battery 106. Battery 106 includes an encasement 112, a feed-through terminal 118, a fill port 181 (partially shown), a liquid electrolyte 116, and an electrode assembly 114. Encasement 112, formed by a cover 140A and a case 140B, houses electrode assembly 114 with electrolyte 116. Feed-through assembly 118, formed by pin 123, insulator member 113, and ferrule 121, is electrically connected to jumper pin 125B. The connection between pin 123 and jumper pin 125B allows delivery of positive charge from electrode assembly 114 to electronic components outside of battery 106.

Figure 2:
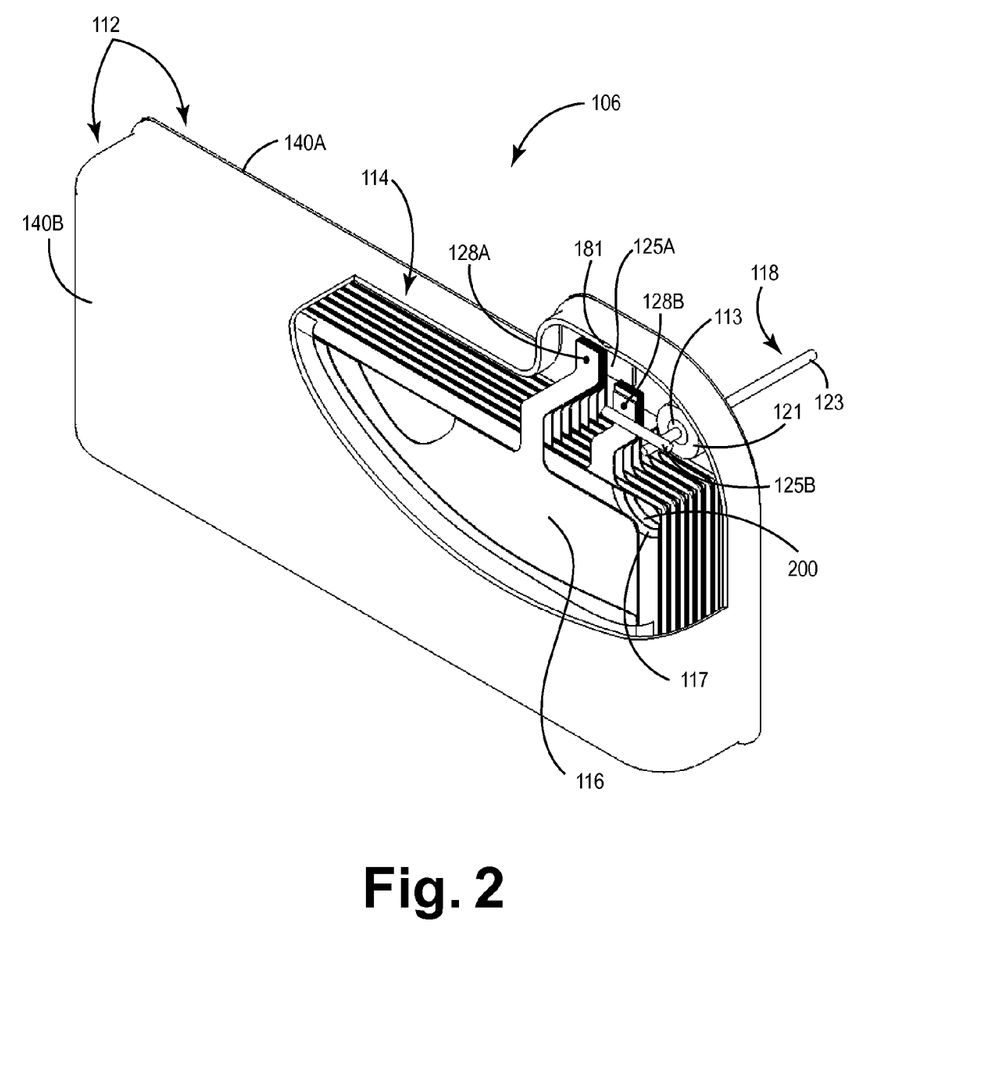
FIG. 2 is a cutaway perspective view of a battery (or cell) in the IMD of FIG. 1.

Fill port 181 (partially shown) allows introduction of liquid electrolyte 116 to electrode assembly 114. Electrolyte 116 creates an ionic path between anode 115 and cathode 119 of electrode assembly 114. Electrolyte 116 serves as a medium for migration of ions between anode 115 and cathode 119 during an electrochemical reaction with these electrodes.

Figure 3A:
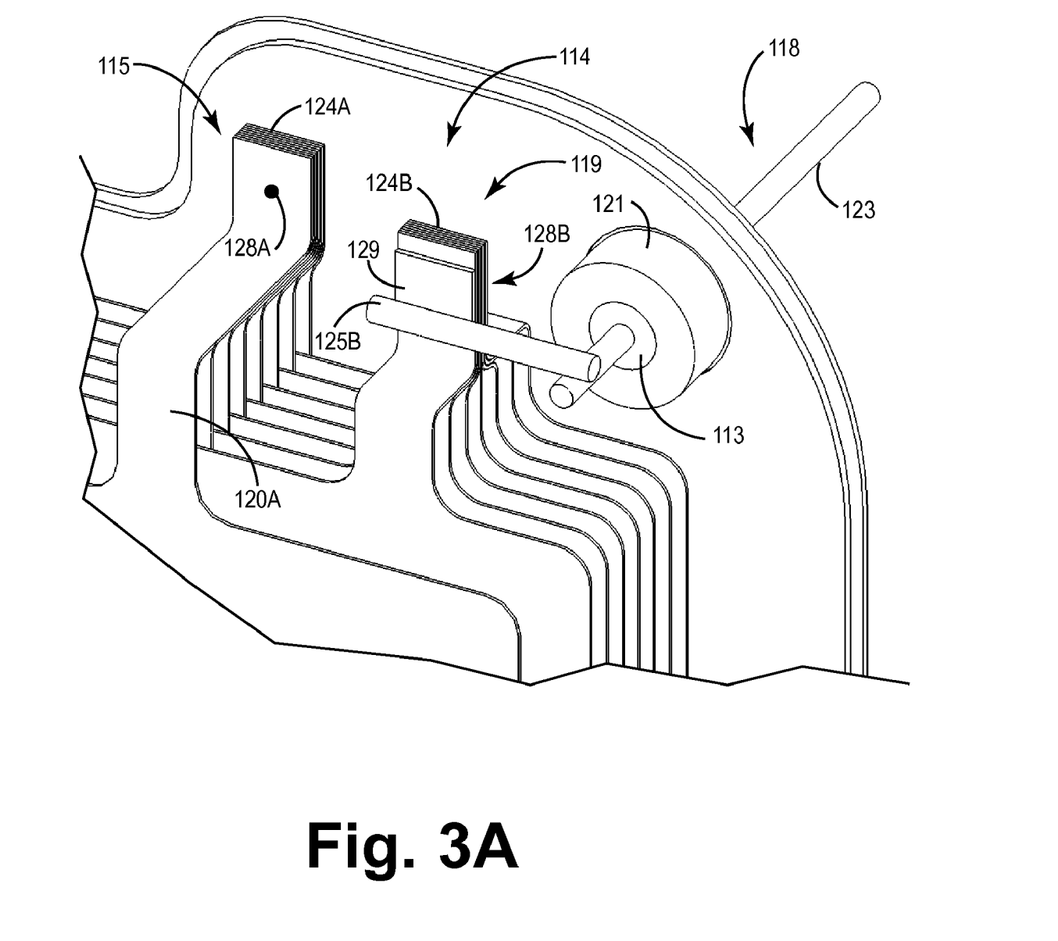
FIG. 3A is an enlarged view of a portion of an electrode assembly depicted in FIG. 2.
Figure 3B:
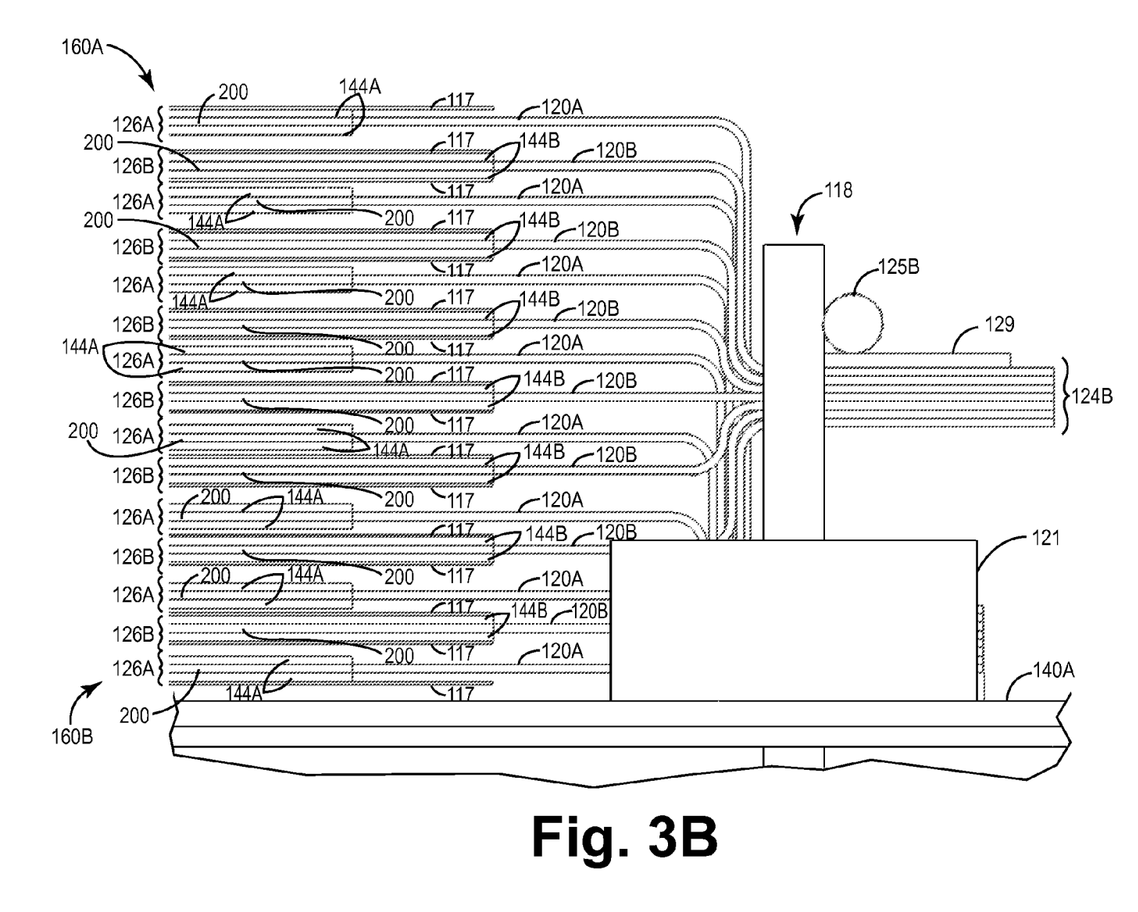
FIG. 3B is a cross-sectional view of a portion of an electrode assembly depicted in FIG. 2.

Referring to FIGS. 3A-3B, electrode assembly 114 is depicted as a stacked assembly. Anode 115 comprises a set of electrode plates 126A (i.e. anode electrode plates) with a set of tabs 124A that are conductively coupled via a conductive coupler 128A (also referred to as an anode collector). Conductive coupler 128A may be a weld or a separate coupling member. Optionally, conductive coupler 128A is connected to an anode interconnect jumper 125A, as shown in FIG. 2.

Each electrode plate 126A includes a current collector 200 or grid, a tab 120A extending therefrom, and electrode material 144A. Tab 120A comprises conductive material (e.g. copper, etc.). Electrode material 144A includes elements from Group IA, IIA or IIIB of the periodic table of elements (e.g. lithium, sodium, potassium, etc.), alloys thereof, intermetallic compounds (e.g. Li—Si, Li—B, Li—Si—B etc.), or an alkali metal (e.g. lithium, etc.) in metallic form. As shown in FIG. 3B, a separator 117 is coupled to electrode material 144A at the top and bottom 160A-B electrode plates 126A, respectively.

Cathode 119 is constructed in a similar manner as anode 115. Cathode 119 includes a set of electrode plates 126B (i.e. cathode electrode plates), a set of tabs 124B, and a conductive coupler 128B connecting set of tabs 124B. Conductive coupler 128B or cathode collector is connected to conductive member 129 and jumper pin 125B. Conductive member 129, shaped as a plate, comprises titanium, aluminum/titanium clad metal or other suitable materials. Jumper pin 125B is also connected to feed-through assembly 118, which allows cathode 119 to deliver positive charge to electronic components outside of battery 106. Separator 117 is coupled to each cathode electrode plate 126B.

Each cathode electrode plate 126B includes a current collector 200 or grid, electrode material 144B and a tab 120B extending therefrom. Tab 120B comprises conductive material (e.g. aluminum etc.). Electrode material 144B or cathode material includes metal oxides (e.g. vanadium oxide, silver vanadium oxide (SVO), manganese dioxide etc.), carbon monofluoride and hybrids thereof (e.g., $CF_x+MnO_2$), combination silver vanadium oxide (CSVO), lithium ion, other rechargeable chemistries, or other suitable compounds.

Figure 4A:
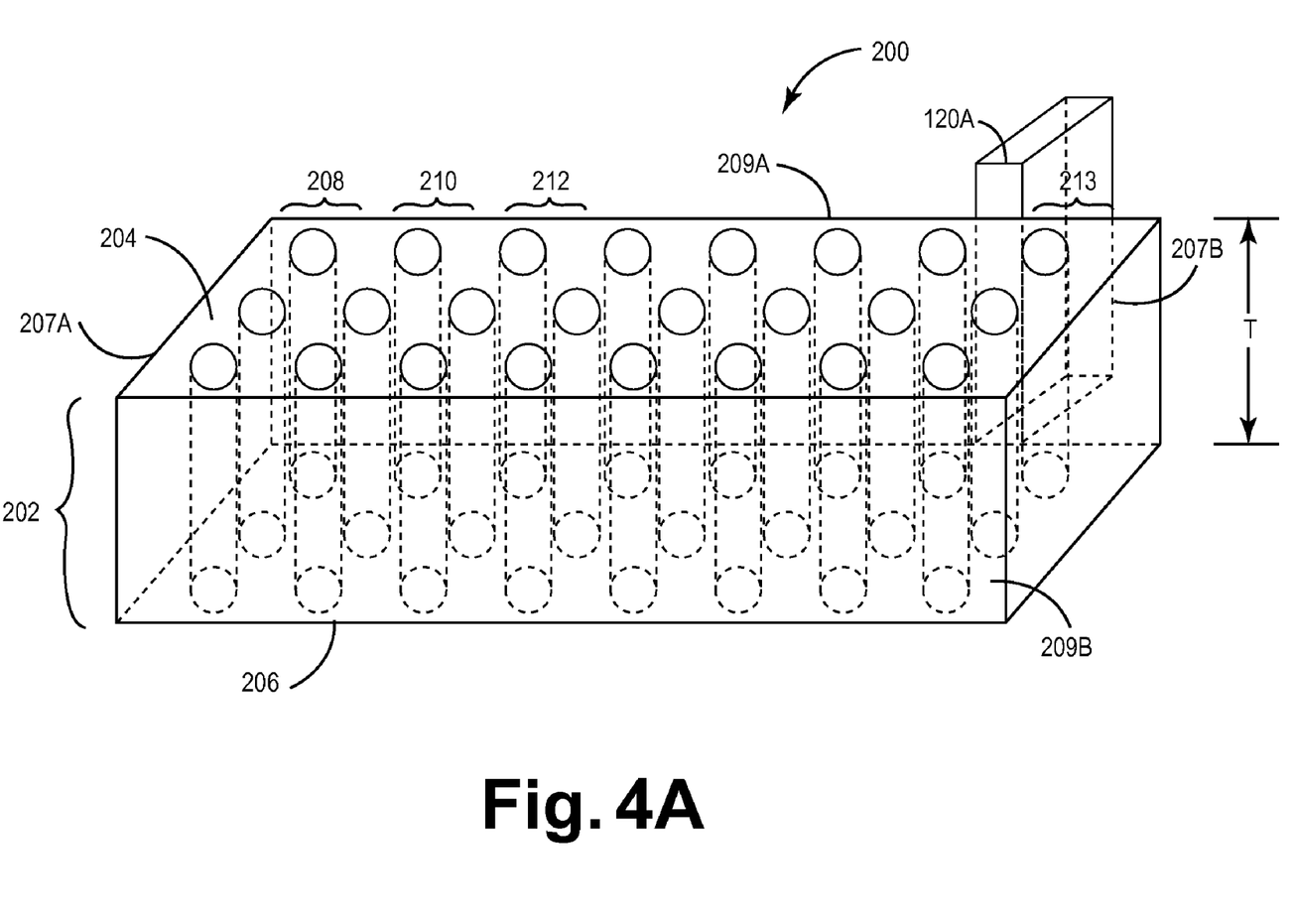
FIG. 4A is an angled cross-sectional view of a current collector in an electrode plate of the electrode assembly depicted in FIG. 3A.
Figure 4B:
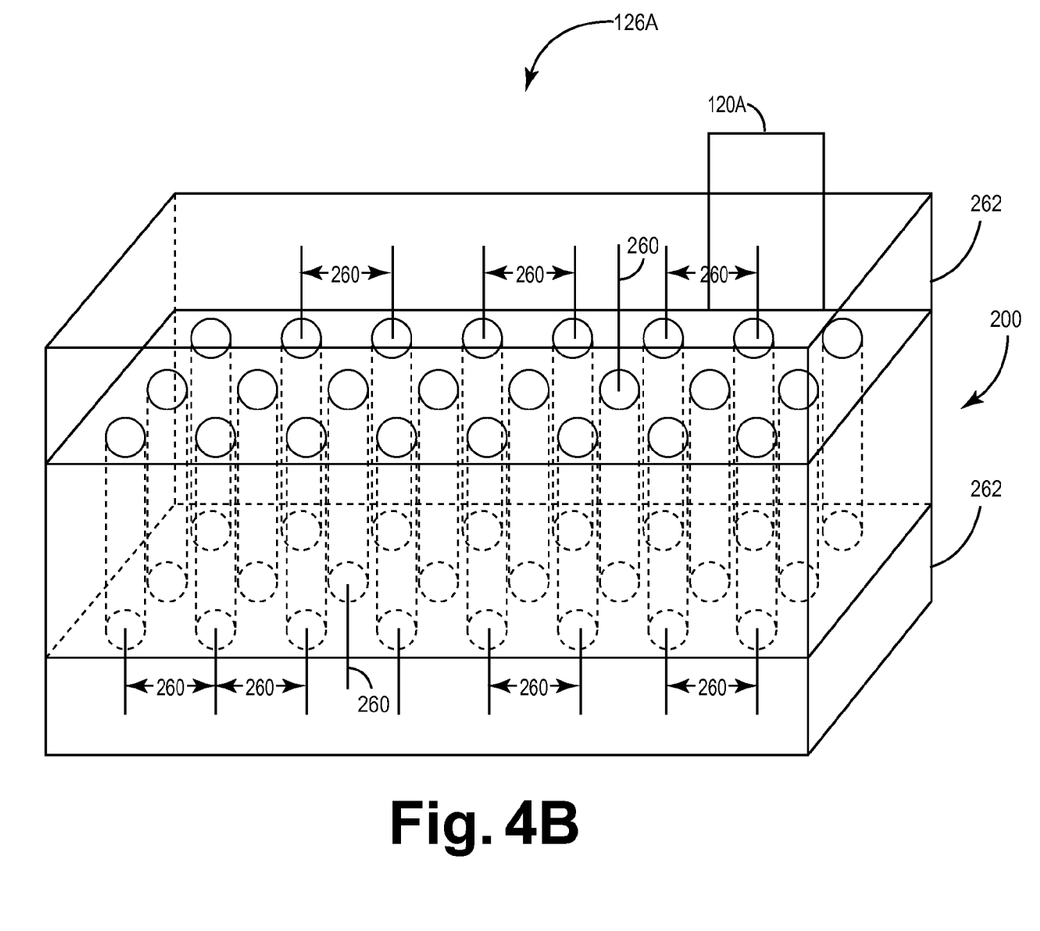
FIG. 4B is an angled cross-sectional view of the electrode plate that includes the current collector depicted in FIG. 4A along with electrode material disposed thereon.
Figure 5:
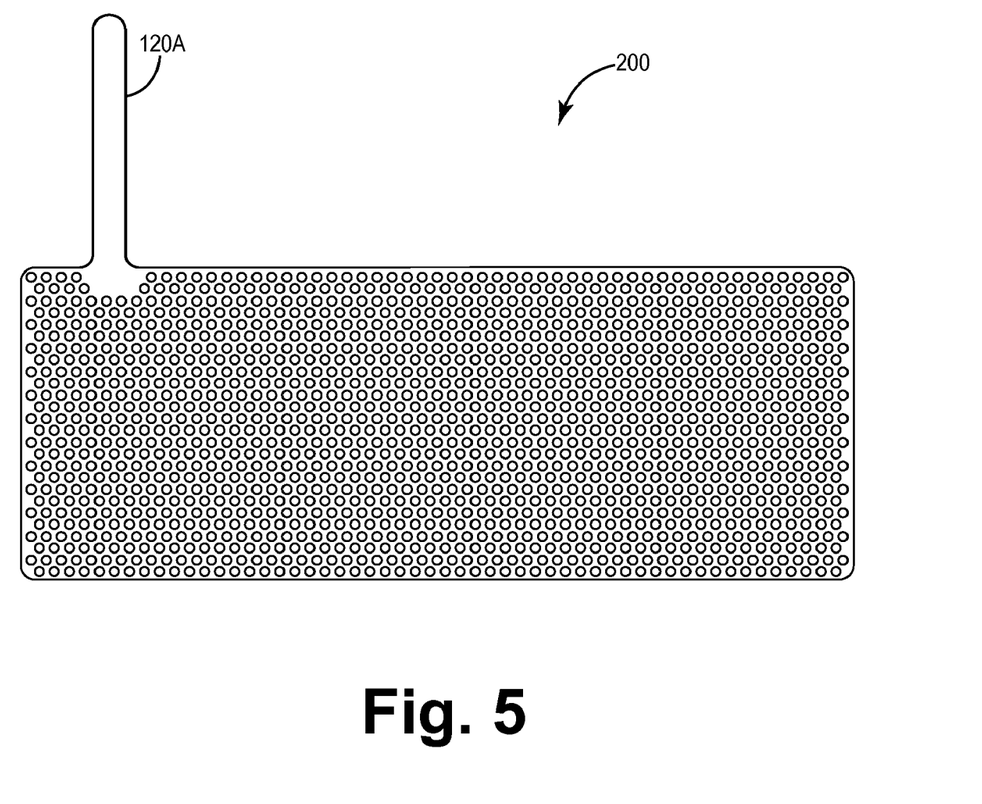
FIG. 5 is a top view of a current collector.

FIGS. 4A-4B and 5 depict details of current collector 200. Current collector 200 is a conductive layer 202 that includes a sides 207A, 207B, 209A, 209B, a first surface 204 and a second surface 206 with a connector tab 120A protruding therefrom. A first, second, third, and N set of apertures 208, 210, 212, 213, respectively, extend from first surface 204 through second surface 206. N set of apertures are any whole number of apertures. Conductive layer 202 may comprise a variety of conductive materials. Current collectors 202 for cathode 119 and tab 120B may be, for example, titanium, aluminum, nickel or other suitable materials. For an anode 115, current collector 200 and tab 120A comprise nickel, titanium, copper an alloy thereof or other suitable conductive material.

Referring to FIG. 4B, apertures 208, 210, 212, 213 in current collector 200 allows electrode material 262 (i.e. electrode material 144A or electrode material 144B) to electrostatically interact to form bonds 260. Bonds 260 ensure that electrode material 262 does not delaminate from current collector 200.

One embodiment of the claimed invention relates to an asymmetric aperture patterns in a current collector 500 that uniformly dissipates heat generated during discharge. Discharge occurs when the battery supplies current to an external circuit or internally to the battery (e.g. during an internal short). Discharge relates to an event which causes current to pass from tab 120A to the perimeter of current collector 500. An event occurs when therapy (e.g. defibrillation, sensing, pacing, etc.) is delivered to a patient or a short exists that is external or internal to the battery. Heat generated in the web is proportional to the square of the current in a specified area. Web is a portion of the current collector (likely narrow) that is between perforations or holes. The claimed invention avoids or eliminates one web having a current density ten times higher than a neighboring web, which may occur in some conventional current collectors. A web is a solid portion of current collector 300 that exists between two apertures.

One embodiment of the asymmetric aperture pattern in current collector 500, shown relative to FIGS. 6A-E, relates to a computer implemented method. In this embodiment, the apertures are the same size throughout current collector 500. The computer implemented method automatically determines an optimized location for each aperture 502 in current collector 500 to uniformly dissipate heat generated during discharge. The computer implemented method involves a computer program, stored on a data storage device (i.e. memory), and executed on a processor of the computer (not shown). A data storage device is a device for recording (i.e. storing) information (i.e. data). A device that only stores data is a recording medium. Devices that process information (data storage equipment) may either access a separate portable (removable) recording medium (e.g. DVD, CD, diskette etc.) or a permanent component to store and retrieve information therefrom.

Figure 6A:
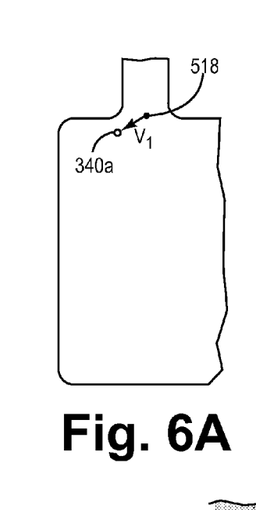
FIGS. 6A-6E are top views of a current collector being formed with a variable aperture pattern that uniformly dissipates current density throughout the current collector.
Figure 6B:
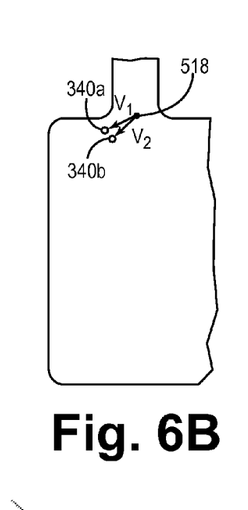
Figure 6C:
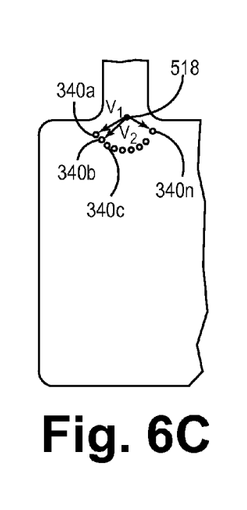
Figure 6D:
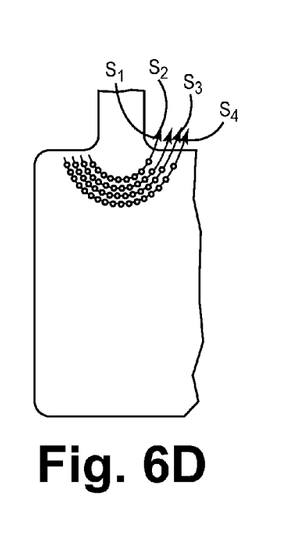
Figure 6E:
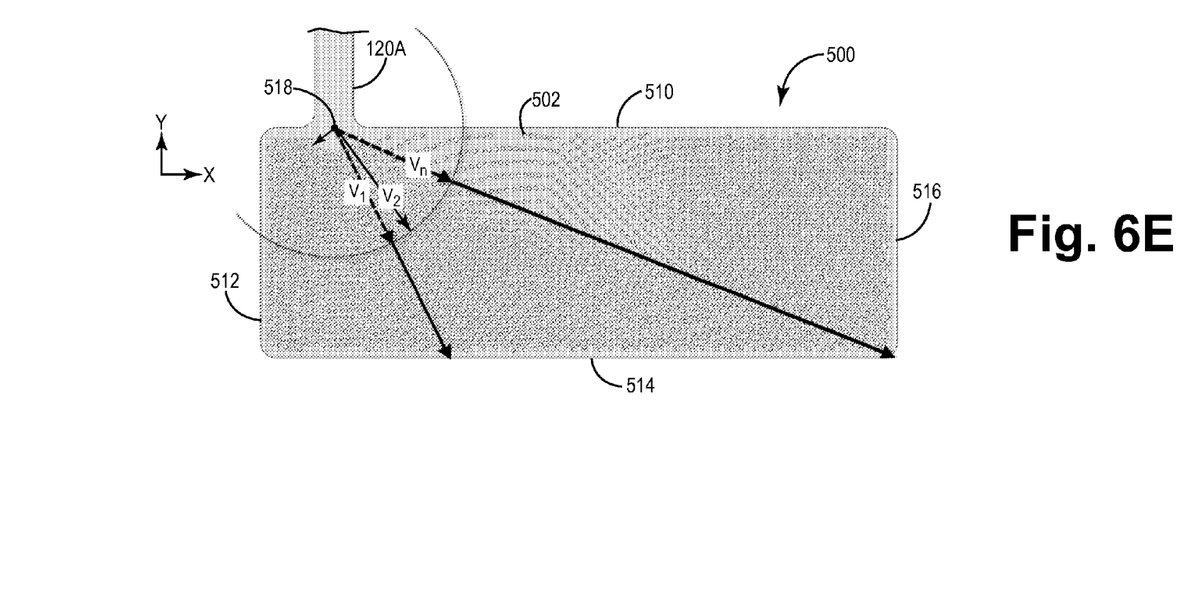
Figure 7:
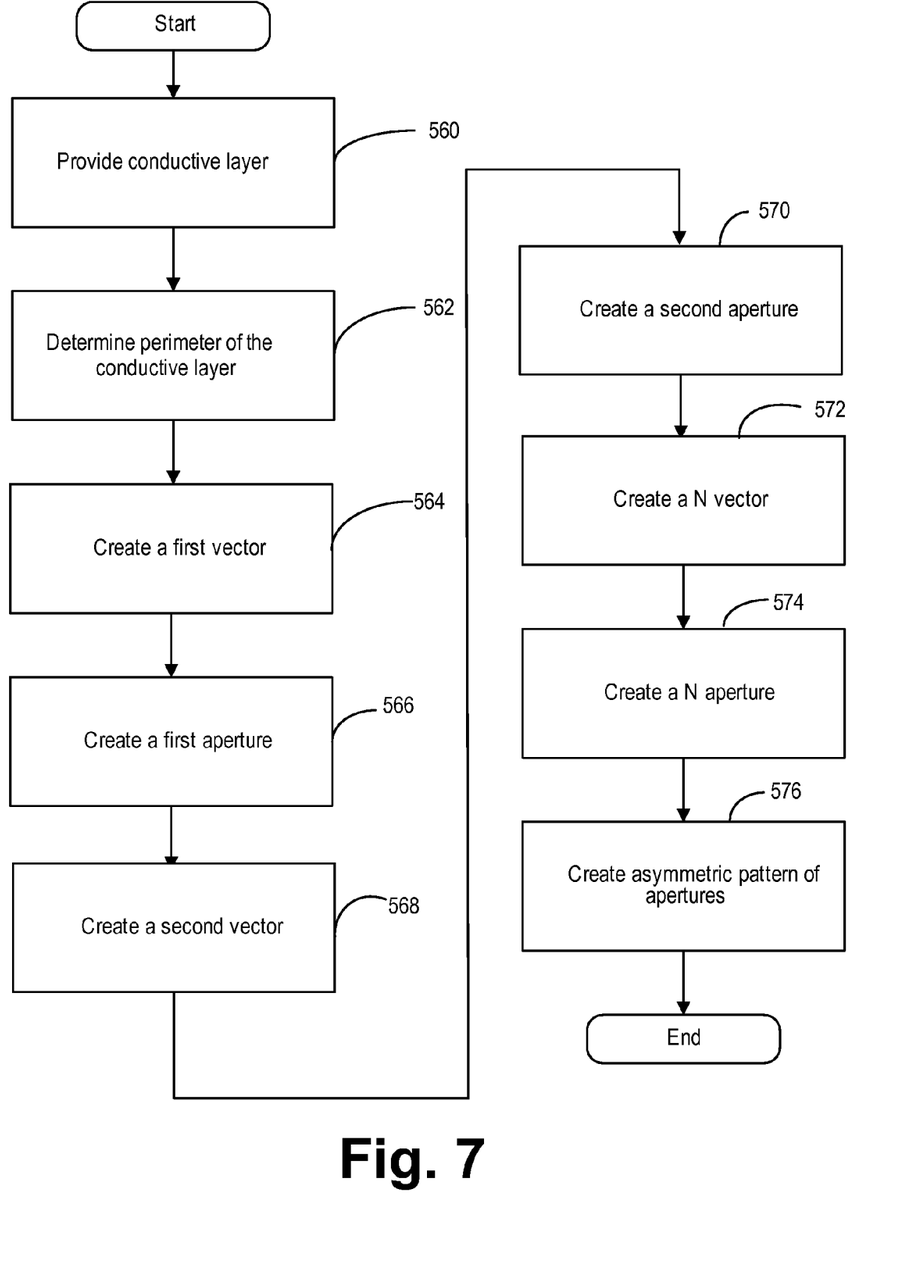
FIG. 7 is a flow diagram of a current collector with an asymmetric aperture pattern.

Referring to FIGS. 6A-7 and a computer program, a method is depicted of an operation for creating a variable or asymmetric pattern of apertures 502 in a current collector 500. At operation 560, a conductive layer is provided. The conductive layer is defined by at least a first, second, third, and fourth end 510, 512, 514, 516. A tab 120A extends from the first end 510. The perimeter of the conductive layer is determined at block 562. The perimeter of the conductive layer is defined as extending to first, second, third, and fourth ends 510, 512, 514, 516 and includes tab 120A. Specifically, a maximum distance from a center point 518 disposed near tab 120A to the first, second, third, and fourth ends 510, 512, 514, 516 is used to determine perimeter. In order to determine the perimeter of current collector 500, center point 518 is pre-selected. For example, in the computer program related to a rectangular current collector, center point 518 possesses coordinates (x, y) where x is 0.192 inches and y=0.60 inches. An initial radius (r1) is predetermined (e.g. 0.0005 inches) for apertures 502. An initial arc, defined as j, determines the first distance from center point 518 in which apertures may be formed from tab 120A. Thereafter, a first distance from the center point 518 to a first location for forming an aperture 502 is determined at block 564. This line segment is the first vector (V1). A vector is a mathematical quantity that is a directed line segment with both a magnitude and direction. A vector is a line designated by its end points (X-Y or X-Y-Z coordinates). In one embodiment, the computer program determines whether the first vector (V1) is directed toward a point on current collector 500 that is acceptable to form an aperture. Specifically, the computer program verifies that the first vector passes conditions to verify that the aperture is within a certain distance of each first, second, third, and fourth ends 510, 512, 514, 516. The conditions also verify that the aperture is within the perimeter of current collector 500. These conditions are a function of an angle between two vectors. For example, If the angle between second end 512 and the vector is $\leq A\tan^{-1}(y/x)$, then the left side (second end 512) distance to the edge=x/Cos(angle). The computer program then checks the second condition. The second condition states that if the angle between third end 514 and the vector is >Atn(y/x) then the third end 514, left of center point 518, is acceptable for placement of an aperture. If the computer program passes this condition, the fourth condition is checked. The fourth condition states that if the angle$\leq$3.1415926/2, the distance to the edge=y/Sin(angle). The fifth condition provides that If the angle$\geq$=3.1415926/2 then end 514, right of center point 518, is acceptable for locating an aperture. The sixth condition states that If the angle$\leq$3.1415926−A$\tan^{-1}(y/(L-x))$ then the distance to the edge=y/Cos(angle−3.1415926/2). The seventh condition states that if the angle is >3.1415926−Atn(y/(L−x)) then end 516's distance to the edge=(L−x)/Cos(3.1415926−angle).

Figure 8:
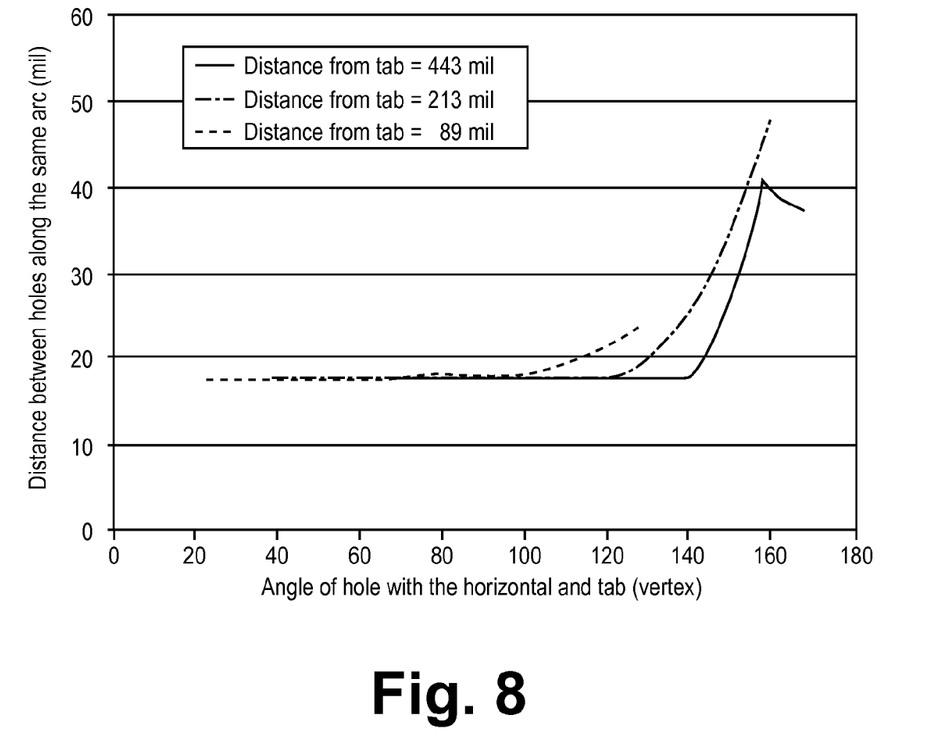
FIG. 8 graphically depicts the distance of apertures along the same arc versus the angle of apertures along the vertex.

If it is determined that the first vector V1 does point to an acceptable location (i.e. within the perimeter and away from the edge of the current collector), a first aperture is created (block 566) the first distance away from center point 518. A second vector (V1) is created (block 568) that extends from center point 518 to a second distance. This vector is also checked against the angle conditions presented above to determine whether the second vector points to an acceptable location in current collector 500. At block 570, a second aperture is created. A N vector (VN) is then created at block 572 that extends from the center point 518 to a N distance. A N aperture is created a N distance away from center point 518 at block 574. As can be seen, this computer program creates apertures in a sweeping motion at block 576. First sweeping motion 1 (S1) creates a first set of apertures; second sweeping motion 1 (S2) creates a second set of apertures; N sweeping motion 1 (SN) creates a N set of apertures; and so on. Referring to FIG. 8, the asymmetric pattern of apertures created during the sweeping operations may depend upon the angle of apertures as it relates to the horizontal and tab (i.e. vertex). Creation of apertures 502 is terminated when an arc length, j, is greater than a distance from center point 518 to a farthest point of the perimeter of the conductive layer.

Figure 9A:
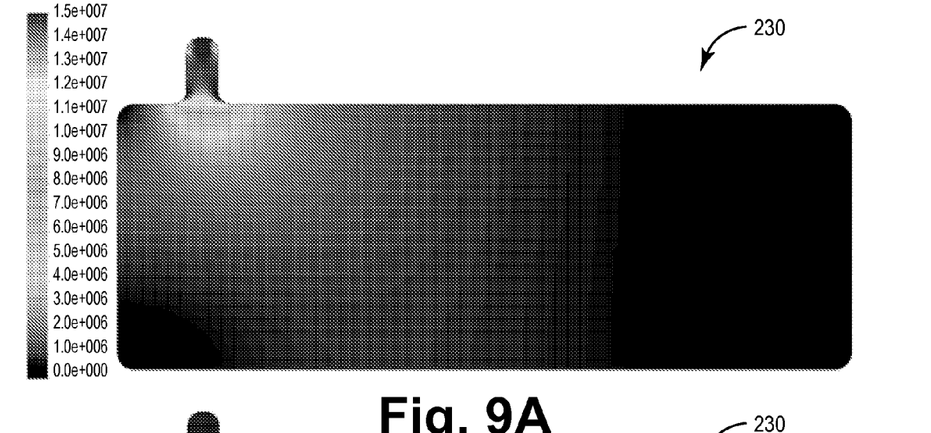
FIGS. 9A-9C depict current density during current flow in a conventional conductive layer without apertures.
Figure 9B:
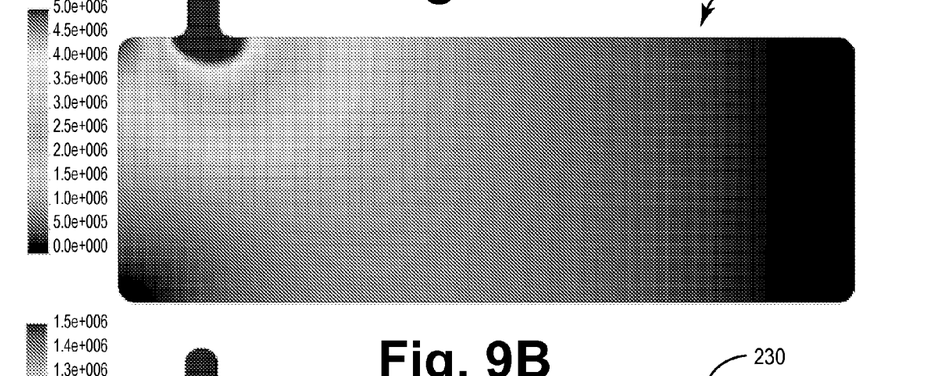
Figure 9C:
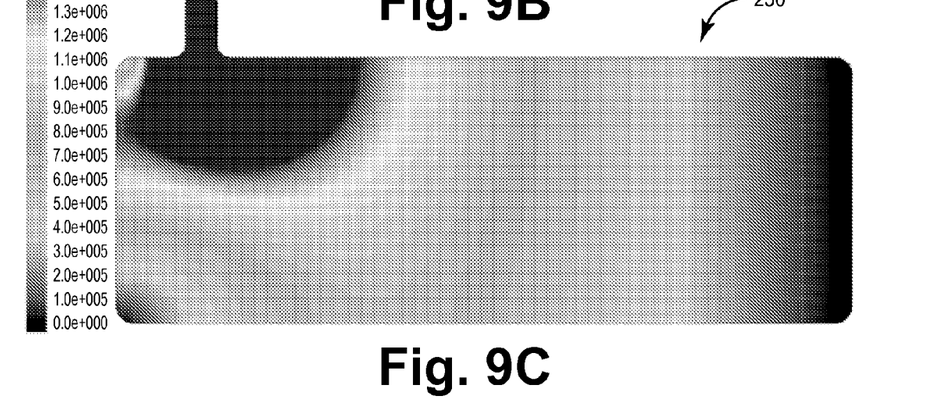
Figure 10A:
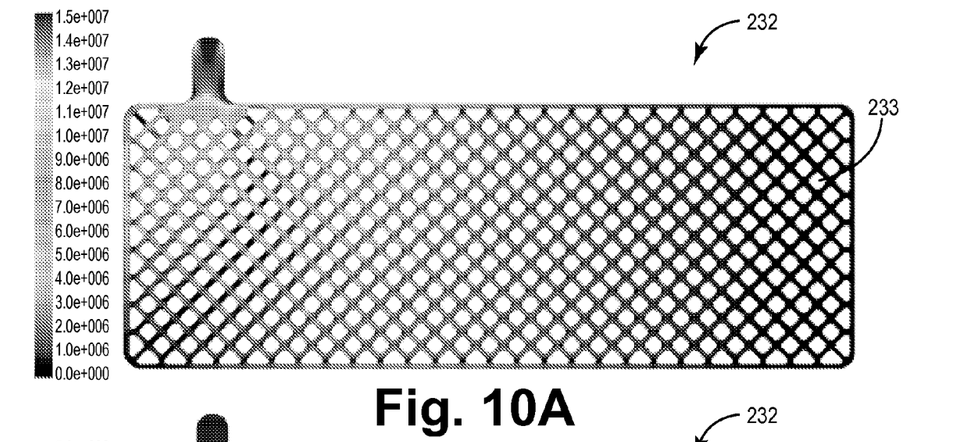
FIGS. 10A-10C depict current density during current flow in a conventional current collector with large uniformly spaced apertures.
Figure 10B:
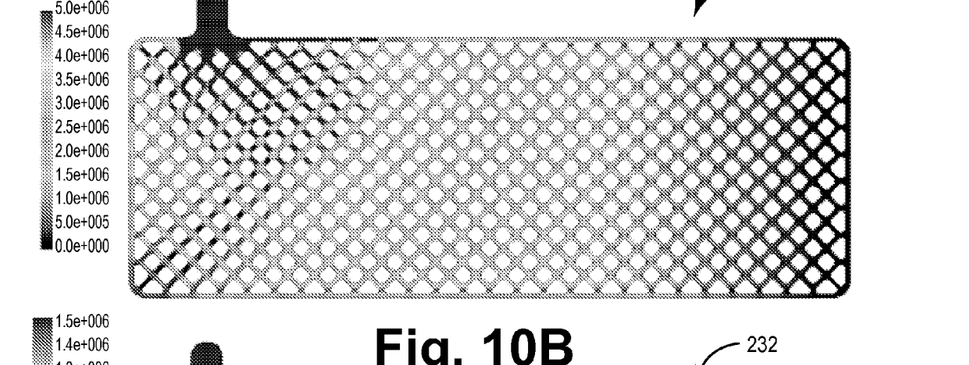
Figure 10C:
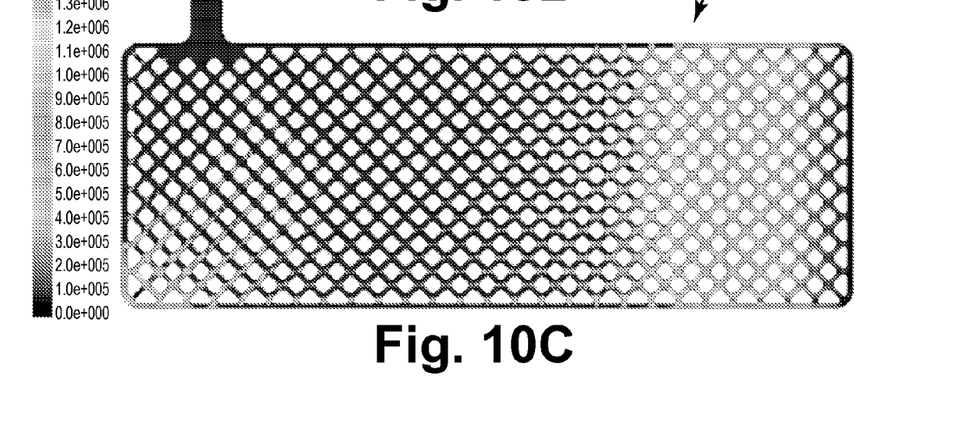
Figure 11A:
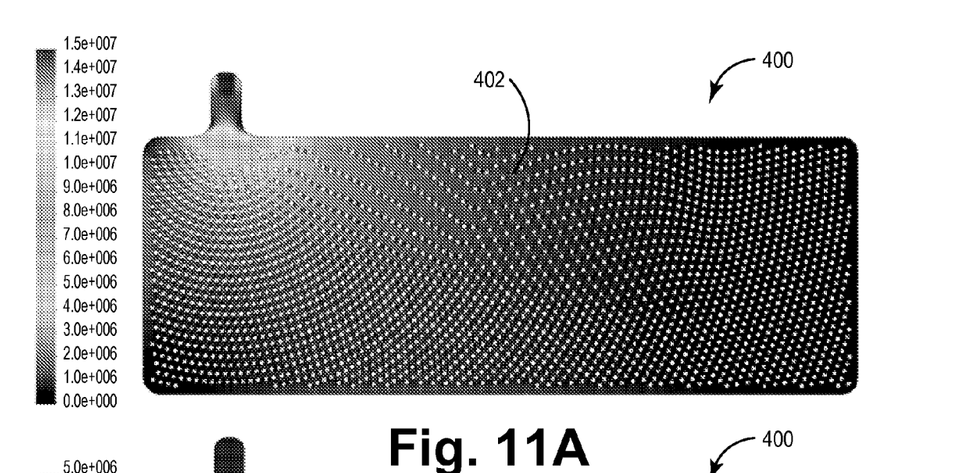
FIGS. 11A-11C depict current density during current flow in a current collector with small variably spaced apertures.
Figure 11B:
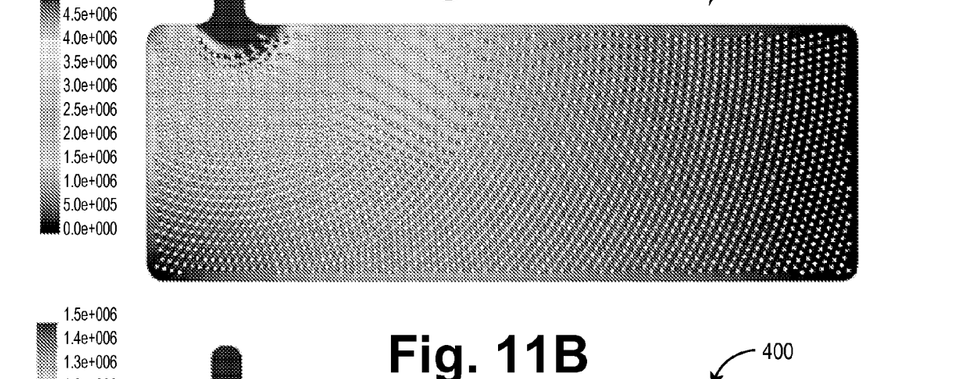
Figure 11C:
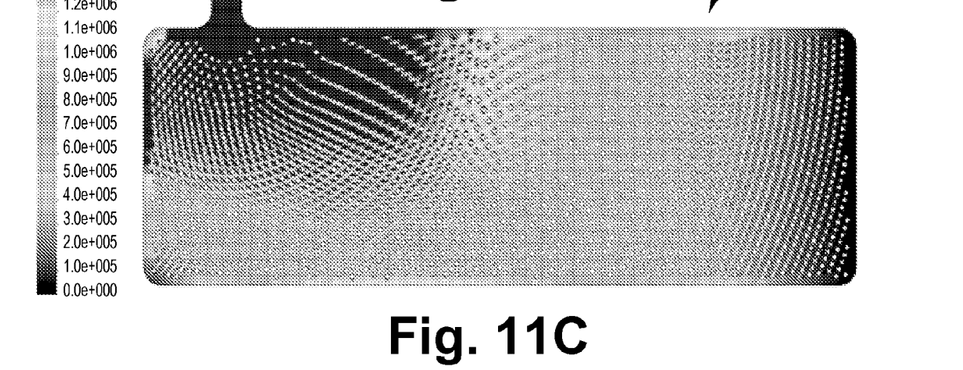

As depicted in FIGS. 11A-11C, current density of the claimed invention is more uniformly spread in current collector 500 compared to conventional current collectors depicted in FIGS. 10A-10C. Indeed, FIGS. 11A-11C reflects uniform heat transfer more closely to the ideal heat transfer of conductive layer depicted in FIGS. 9A-9C. Referring to vector V1' and vector V2', less current is carried, as shown by the area shaded between these two vectors. In contrast, the areas between V3', and V5' is larger which allows more current to flow between apertures 550, and 552.

Figure 12:
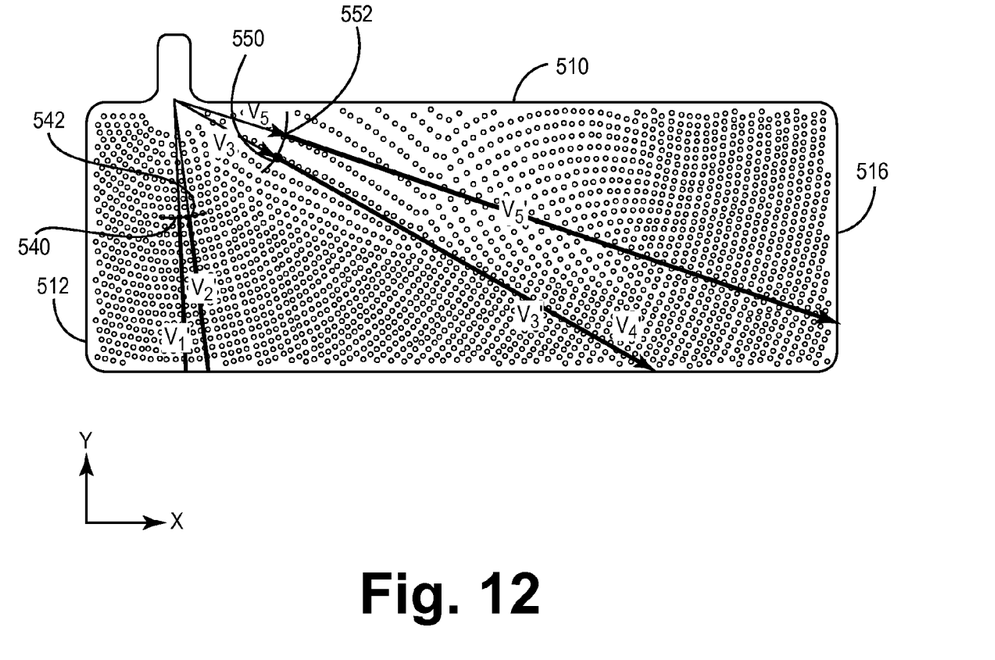
FIG. 12 is a top view of a current collector that depicts current flow along different vectors.

V3' is larger than V1' due to the geometry of current collector 500. As shown, the starting points for V3', and V5' are the end points of vectors V3, and V5. Thus, the angle between vectors V3', and V5' is larger than the angle between V1' and vector V2'.

The angle between vectors is a function of, and increases with, the distance from the N aperture to the perimeter edge of current collector 500 along the N vector. Longer distances such as V3' in a vector allows more current to be carried from the current collector 500 to tab 120A and thus results in a larger angle between aperture vectors. The range an angle between two neighboring apertures can be between 0 and 90 degrees. When the calculated angle between holes is too small, a minimum distance exists between apertures to ensure that there is enough structural integrity of the current collector 500. This minimum distance occurs close to the current collector's 500 perimeter edge where the current density expected to pass between the two apertures is low. There is also a minimum distance between an aperture and the edge of the current collector 500 which cannot be less than 15 thousands of an inch. Generally, no maximum distance exists between apertures along an arc S1, S2, etc. There is a specified distance between arcs S1 and S2, S2 and S3, etc. Minimizing this distance will result in better adhesion of the active material to the current collector 500. The lower limit of the minimum distance between apertures seeks to maintain structural integrity of each web in the current collector 500. (e.g. 0.008 inches (in)), the angle between the N vector and N−1 vector is a function of the distance from the tab to the apertures.

Increased spacing between apertures 502 allows for increased current to be carried due to a more direct current flow path and less heat (i.e. lower temperature) in current collector 500. Increased spacing between apertures 502 balances the current density throughout current collector 500, reduces heat generation, thereby reducing the temperature rise in the current collector 500. Additionally, resistance in current collector 500 is reduced. For example, temperature (e.g. 500 degrees Celcius) in the current collector 500 is a function of the heat generation as well as heat transfer to the rest of the cell or battery. A tenfold (i.e. 10 times) increase in current density could result in an increase in temperature of 500 degrees Celcius. Lower current collector resistances reduces the overall battery resistance. An increase in temperature of 500 degrees Celcius above room temperature will about double the resistance for a titanium current collector. This also can result in lower electrode areas and thus lower battery volumes.

The local current density in the collector is optimized so that "hot spots" or areas of high current density can be reduced or eliminated. An optimized collector possesses reduced thickness. A reduction in heat generation of four times, for example, could be achieved in optimizing the hole pattern. The same hole or aperture pattern could provide an about two times reduction in heat generation in a collector that is half the thickness. If a two times heat reduction is acceptable, then reducing the thickness will result in a increase in energy density of the battery. In each current collector 500, apertures 502 are placed in a circular pattern with the center of the circle disposed at tab 120A. Current flows more directly between the tab and current collector 500.

The description of the invention is merely exemplary in nature and, thus, variations that do not depart from the gist of the invention are intended to be within the scope of the invention. Such variations are not to be regarded as a departure from the spirit and scope of the invention. For example, while several embodiments include specific dimensions, skilled artisans appreciate that these values will change depending, for example, on the shape of a particular element.

The invention claimed is:

1. A battery for an implantable medical device comprising:
    an anode that comprises a first set of electrodes, each electrode including a current collector with anodic material disposed thereon;
    a cathode that comprises a second set of electrodes, each electrode including a current collector with cathodic material disposed thereon, wherein each electrode comprises a current collector that includes an asymmetric aperture pattern in which each aperture is the same size, wherein the asymmetric aperture pattern comprises a plurality of sets of apertures, wherein each set of apertures is defined along a corresponding arc of a plurality of arcs, wherein each of the plurality of arcs is defined at a different distance from a center point proximate a tab of the electrode, and further wherein spacing of the set of apertures having the same size is varied along the corresponding arc of the plurality of arcs.

2. The battery of claim 1 wherein a minimum distance between a first aperture and a second aperture is 0.008 inches.

3. The battery of claim 1 wherein a maximum distance between a first aperture and a second aperture is 0.5 inches.

4. The battery of claim 1 wherein variable spacing exists between neighboring apertures in a current collector.

5. A battery for an implantable medical device comprising:
an anode that comprises a first set of electrodes, each electrode including a current collector with anodic material disposed thereon;
a cathode that comprises a second set of electrodes, each electrode including a current collector with cathodic material disposed thereon, wherein each electrode comprises a current collector that includes an asymmetric aperture pattern in which each aperture is the same size, wherein variable spacing exists between neighboring apertures in the current collector, wherein the asymmetric aperture pattern comprises a plurality of sets of apertures, wherein each set of apertures is defined along a corresponding arc of a plurality of arcs, wherein each of the plurality of arcs is defined at a different distance from a center point proximate a tab of the electrode, and further wherein spacing of the set of apertures having the same size is varied along the corresponding arc of the plurality of arcs.

6. A battery for an implantable medical device comprising:
an anode that comprises a first set of electrodes, each electrode including a current collector with anodic material disposed thereon;
a cathode that comprises a second set of electrodes, each electrode including a current collector with cathodic material disposed thereon, wherein each electrode comprises a current collector, each current collector includes a first end, a second end, a third end, a fourth end, and a tab extending from the fourth end, wherein the current collector extends between the second end and the fourth end along a y-axis of the current collector and the current collector extends between the first end and the third end along an x-axis of the current collector, and further wherein apertures are asymmetrically defined in the current collector along both the x-axis and the y-axis and each aperture is the same size, wherein the asymmetrically defined apertures comprise a plurality of sets of apertures, wherein each set of apertures is defined along a corresponding arc of a plurality of arcs, wherein each of the plurality of arcs is defined at a different distance from a center point proximate the tab of the electrode, and further wherein spacing of the set of apertures having the same size is varied along the corresponding arc of the plurality of arcs.

7. A battery for an implantable medical device comprising:
an anode that comprises a first set of electrodes, each electrode including a current collector with anodic material disposed thereon;
a cathode that comprises a second set of electrodes, each electrode including a current collector with cathodic material disposed thereon, wherein each electrode comprises a current collector, each current collector includes a first end, a second end, a third end, a fourth end, and a tab extending from the fourth end, wherein a plurality of sets of apertures having the same size are defined in each electrode, wherein each set of apertures is defined along a corresponding arc of a plurality of arcs, wherein each of the plurality of arcs is defined at a different distance from a center point proximate the tab of the electrode, and further wherein spacing of the set of apertures having the same size is varied along the corresponding arc of the plurality of arcs, and further wherein the apertures are arranged such that spacing of a plurality of adjacent apertures along at least a portion of the current collector from the first end to the third end along the x-axis is different than spacing of another plurality of adjacent apertures along a portion of the current collector from the first end to the third end and such that spacing of a plurality of adjacent apertures along at least a portion of the current collector from the second end to the fourth end along the y-axis is different than spacing of another plurality of adjacent apertures along at least a portion of the current collector from the second end to the fourth end along the y-axis.

8. The battery of claim 7, wherein each of the plurality of arcs is separated from adjacent arcs by a same distance.

9. The battery of claim 1, wherein each of the plurality of arcs is separated from adjacent arcs by a same distance.

10. The battery of claim 5, wherein each of the plurality of arcs is separated from adjacent arcs by a same distance.

11. The battery of claim 6, wherein each of the plurality of arcs is separated from adjacent arcs by a same distance.

* * * * *